(12) United States Patent
Falco

(10) Patent No.: US 6,695,093 B1
(45) Date of Patent: Feb. 24, 2004

(54) EARPLUG

(75) Inventor: Robert Falco, Indianapolis, IN (US)

(73) Assignee: Aearo Company, Sturbridge, MA (US)

( * ) Notice: Subject to any disclaimer, the term of this patent is extended or adjusted under 35 U.S.C. 154(b) by 236 days.

(21) Appl. No.: 09/482,237

(22) Filed: Jan. 13, 2000

(51) Int. Cl.[7] ............................. A61B 7/02; H04R 25/02
(52) U.S. Cl. ........................................ 181/135; 181/130
(58) Field of Search ................................ 181/135, 134, 181/130, 129, 294; D24/106, 174; D29/112; 128/864, 865, 867

(56) References Cited

U.S. PATENT DOCUMENTS

| | | | |
|---|---|---|---|
| 2,246,736 A | * 6/1941 | Knudsen | 128/152 |
| 2,538,339 A | 1/1951 | Thomas | |
| 2,573,923 A | * 11/1951 | Mezz | 128/151 |
| 2,934,160 A | * 4/1960 | Touson | 181/23 |
| 3,800,791 A | 4/1974 | Visor | |
| RE29,487 E | 12/1977 | Gardner, Jr. | |
| 4,158,087 A | 6/1979 | Wood | |
| D253,723 S | 12/1979 | Leight | |
| 4,219,018 A | 8/1980 | Draper, Jr. | |
| 4,237,176 A | * 12/1980 | Brueggemann et al. | 428/212 |
| 4,461,290 A | * 7/1984 | Gardner, Jr. et al. | 128/152 |
| 4,867,149 A | 9/1989 | Falco | |
| 4,936,411 A | 6/1990 | Leonard | |
| 5,074,375 A | * 12/1991 | Grozil | 181/135 |
| 5,203,352 A | 4/1993 | Gardner, Jr. | |
| 5,249,309 A | 10/1993 | Berg et al. | |
| D369,655 S | 5/1996 | Esler et al. | |
| D375,551 S | 11/1996 | Esler et al. | |
| 5,792,998 A | 8/1998 | Gardner, Jr. et al. | |
| 5,809,574 A | 9/1998 | Falco et al. | |
| 5,811,742 A | * 9/1998 | Leight | 181/135 |
| 5,957,136 A | 9/1999 | Magidson et al. | |
| 5,988,313 A | * 11/1999 | Hakansson | 181/135 |
| 6,006,857 A | * 12/1999 | Leight et al. | 181/135 |

FOREIGN PATENT DOCUMENTS

| | | | | |
|---|---|---|---|---|
| DE | 33 04 362 A1 | * 8/1984 | | A61F/11/00 |
| DE | 35 36 793 A1 | * 4/1987 | | A61F/11/02 |
| JP | 8-275298 | * 10/1996 | | H04R/25/02 |

* cited by examiner

*Primary Examiner*—Robert Nappi
*Assistant Examiner*—Edgardo San Martin
(74) *Attorney, Agent, or Firm*—Cantor Colburn LLP

(57) ABSTRACT

The present invention provides an earplug formed of a body and a stem member. The body has an insertion end and an opposing second end and further includes a stem channel formed therein. The stem member is disposed within the stem channel of the body so, as to securely couple the stem member to the body for easy insertion of the earplug into an ear of the wearer. According to the present invention, the stem member is formed of a material such that insertion of the earplug into the ear results in the stiffness of the stem member decreasing such that the stem member becomes less stiff upon being inserted and positioned within the ear. Advantageously, the design and/or material of the stem member permits the earplug to be stiff for insertion thereof into the ear; however, the preferred material used to form the stem member exhibits a softening characteristic such that upon insertion into the ear, the stem member softens. In other words, the stem member relaxes and relieves any excess pressure caused by the insertion of the earplug into the ear.

28 Claims, 2 Drawing Sheets

EARPLUG

BACKGROUND OF THE INVENTION

1. Field of the Invention

This invention relates generally to hearing protective devices and is more specifically directed to an earplug construction useful as a hearing protector.

2. Brief Discussion of the Prior Art

Environmental sounds are typically comprised of a mixture of various sound wave frequencies having varying intensities. It is well documented that repeated or prolonged exposure to sounds of sufficiently high sound pressure level will cause temporary or permanent hearing loss. For example, exposure to sound waves of some frequencies and of varying intensities under conditions of severe impact can damage the auditory organ and cause serious hearing problems, including deafness. Injurious noises such as those caused by explosions or bursts are often comprised of a mixture of sound wave frequencies of varying intensity. These disturbing frequencies are in both the high and low frequency bands and have an intensity sufficient to cause hearing problems. Individuals who are frequently exposed to sound having such disturbing and sometimes dangerous frequencies and intensities run the risk of incurring such injuries as hearing loss or even deafness. These individuals include workers at demolition or construction sites, operators of heavy, noisy equipment and those in active military service. Ear (i.e. hearing) protection is needed to prevent a loss in hearing acuity and the gradual decrease in the threshold of hearing resulting from extended exposures to loud noise.

Sound attenuation devices are known which specifically address this problem. These include conventional earplugs, earmuffs, and the like which function to reduce the negative effects of exposure to dangerous frequencies by limiting the entry of all sound waves into the auditory organ. Typically, pre molded earplugs were made to offer the user a simple comfortable way to protect against harmful or unwanted noise. Pre molded earplugs progressed from single flange designs fitting one size, i.e., small, medium, or large, etc. As time progressed, these pre molded earplugs improved and the earplugs included multiple flanges covering a wider range of sizes an earplug would fit and attenuate. Recently, some manufacturers have added stiffeners to their multi flanged pre molded earplugs to aid in insertion, leading to improved fit and attenuation. Conventially, these insertion tools or stem stifeners have been made in the form of tubes that fit over the flexible stem and also have been in the form of stiff cylindrical inserts placed inside the earplug stem.

SUMMARY

The above-described drawbacks and deficiencies of the prior art are alleviated by the earplug of the present invention. The earplug includes a body having a stem channel formed therein and a stem member disposed within the stem channel. According to the present invention, the stem member is formed of a material such that insertion of the earplug in an ear of a user results in the stiffness of the stem member decreasing such that at least the portion of the stem member which is inserted into the ear becomes less stiff upon being inserted and positioned within the ear.

In one embodiment, the body includes a stalk member having multiple flange elements extending therefrom and the stem member is disposed within the stem channel formed in the stalk member. Preferably, the stalk member includes an array of at least three rearwardly directed and spaced apart flange elements, wherein the first of the flange elements extends from a nose end of the stalk member. Preferably, each of the flange elements has a generally hemispherical cross section and each of the flange elements of the array includes a skirt of relatively thin uniform thickness and is composed of a soft resilient polymeric material. The soft resilient polymeric material preferably has a Shore A Durometer hardness value of between about 10 and about 90. The flange elements of the array increase serially in diameter, starting from the nose end of the stalk member.

The stem channel preferably has a first section and a second section in a first embodiment, wherein the stem member is securely disposed within the stem channel. in a frictional manner. In the exemplary embodiment, the stem member comprises an elongated member having a first end and an opposing second end. The first end comprises a paddle portion which permits a user to easily grip the stem member for inserting the earplug into an ear canal. The second end of the stem member comprises a retaining portion to aid in retaining the stem member within the stalk member. Between the paddle portion and the ball portion, the stem member includes a tapered shaft having a varying diameter. In the illustrated embodiment, the shaft has a greater diameter closer to the paddle portion and the taper of the shaft leads to a smaller diameter at the ball portion of the stem member.

According to the present invention, the stem member is formed of a material having a glass transition in the temperature range of about 50° F. to about 100° F. and preferably from about 80° F. to about 100° F. This material preferably exhibits noticeable property changes in hardness, flexability, and elastic modulus when the temperature of the material is changed. Suitable materials having these characteristics are certain polyurethane and polyvinyl chloride based polymeric materials. These properties advantageously permit the stem member to be both stiff for pushing the earplug into the ear canal and flexible to take the bend of the ear canal after the earplug has been inserted into the ear canal. After the earplug has been inserted into the ear canal, the material of the stem member permits the stem member to soften to a relaxed state and this causes any excess pressure on the ear canal to be released or relieved.

The stem member is inserted into the stem channel so that the paddle portion extends from the end of the stalk member opposite the nose end and the tapered portion of the stem member frictionally engages the first section of the stem channel and the ball portion of the stem member frictionally engages the second section of the stem channel so that the stem member is securely disposed within the stalk member.

In another embodiment, the body comprises a foam body formed from any number of suitable foams and the body may take any number of shapes and sizes.

By employing a stem member having the previously-mentioned characteristics, the earplug of the present invention offers improved ease of insertion and improved attenuation because of the improved fit within the ear canal of the user. The above-discussed and other features of the present invention will be appreciated and understood by those skilled in the art from the following detailed description and drawings.

BRIEF DESCRIPTION OF THE DRAWINGS

Referring to the FIGURES wherein like elements are numbered alike in the several FIGURES.

DESCRIPTION OF THE PREFERRED EMBODIMENTS

Figure 1:
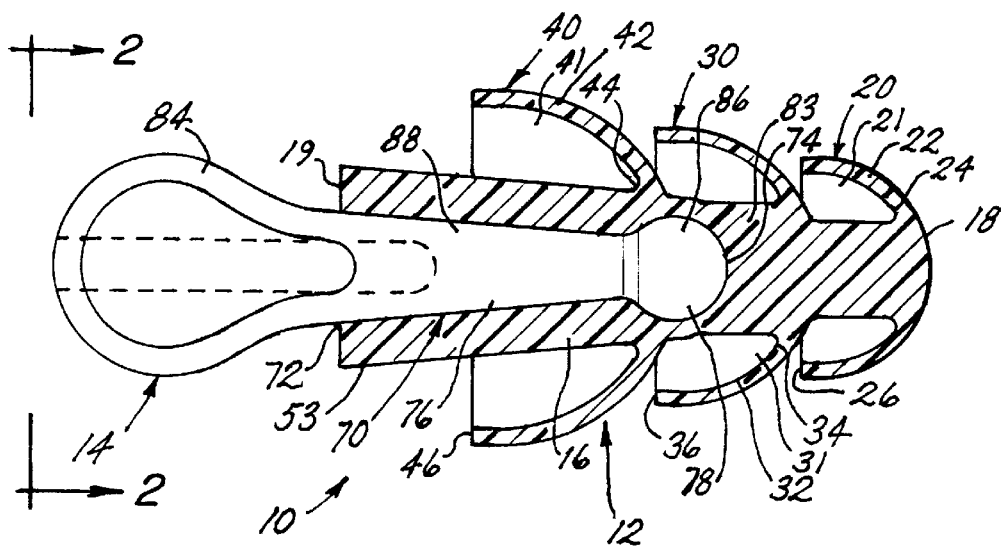
FIG. 1 is a cross sectional view of an earplug according to a first embodiment of the present invention.

According to the present invention, an earplug is provided and is generally shown at 10. The illustrated earplug 10 broadly comprises a body 12 and a stem member 14. An exemplary stalk member 12 is generally disclosed in commonly assigned U.S. Pat. No. 4,867,149, which is hereby incorporated by reference in its entirety. The body 12 is formed of a stalk member 16 which includes an array of at least three rearwardly orientated and spaced flange elements 20, 30, and 40. The stalk member 16 broadly has a nose end 18 and an opposing free end 19. Preferably, each of the flange elements 20, 30, 40 has a generally hemispherical cross section; however, it will be appreciated that other shapes may be used according to the present invention. Preferably, each of flange elements 20, 30, and 40 extends rearwardly from its point of attachment to the stalk member 16 in a convexly arcuate manner. The body 12 of the present invention may be fabricated by any suitable polymer molding technique, such as injection molding thereof. The first flange element 20 extends outwardly and rearwardly from the nose end 18 of the stalk member 16 to define a uniformly flange skirt 22 which is spaced apart along its length from that portion of stalk member 16 lying thereunder. The second flange element 30 extends outwardly and rearwardly from a first intermediate location along the length of the stalk member 16 to thereby define a uniformly thin skirt 32 which is spaced apart along its length from that portion of the stalk member 16 lying thereunder. Similarly, the third flange element 40 extends outwardly and rearwardly from a second intermediate location along the length of the stalk member 16, thereby to define a uniformly thin skirt 42 which is spaced apart along its length from that portion of the stalk member 16 lying thereunder. As illustrated, each of the flange skirts 22 32, and 42 includes a root portion 24, 34, and 44, respectively. Each of the root portions 24, 34, and 44 comprises a point of juncture of the interior surfaces of the skirts 22, 32, 42 with the stalk member 16. The root portions 24, 34, and 44 are preferably conformed such as to provide minimum radiusing therebetween consistent with good molding practices, thereby to minimize thickening and consequential stiffening of the material construction at the juncture points. This design feature of the construction not only assures that the skirts 22, 32, and 42 are afforded maximum flexibility at the root portions 24, 34, and 44, but also provides the skirts 22, 32, and 42 with a desireable "over center" eversion capability whereby each of skirts 22, 32, and 42 can be readily manipulated so as to be everted from its normally rearwardly directed orientation to a forwardly directed orientation. When so forwardly everted, the interior surfaces of the skirts 22, 32, and 42 and the portions of the stalk member 16 normally underlying the skirts 22, 32, and 42 are exposed, thereby affording the user with the ability to readily inspect and/or cleanse areas of the earplug normally hidden from view. Preferably, the spacing between flange elements 20, 30 and 40 along with the stalk member 16 be such that trailing edges 26 and 36 of the skirts 22 and 32, respectively, be coplanar to or, even more preferably, be slightly overlying the nose end of the succeeding flange element thereto. The diameter of that portion of the stalk member 16 underlying each of the skirts 22, 32, and 42, respectively, is selected such as to provide an annular free space 21, 31, or 41 thereunder and into which free space the respective skirt is enabled to deflect during insertion of the earplug 10 into the ear canal. The specific dimensions of the annular free spaces 21, 31, and 41 are not particularly critical provided, of course, that each be adequate to serve the foregoing function.

The stalk member 16 is generally designed to include a taper so that the free end 19 has a greater diameter than a diameter of stalk member 16 proximate the nose end 18. The stalk member 16 further includes a stem channel formed therein and generally indicated at 70. The stem channel 70 is designed to receive and secure the stem member 14. It being understood that the stem channel 70 therefore has a shape which is complementary to the stem member 14.

More specifically, the stem channel 70 has an entrance 72 formed at the free end 19 of the stalk member 16 and a closed end 74 formed within the stalk member 16. The stem channel 70 has a first section 76 which leads from the entrance 72 to a second section 78 which includes the closed end 74. In the exemplary embodiment, the second section 78 has a ball-like configuration and the first section 76 is a tapered channel in which the width at the entrance 72 is greater than a width of the first section 76 at the juncture between the first section 76 and the second section 78 where the first section 76 opens into the second section 78. The stem channel 70 is designed to receive the stem member 14 in a friction fitting manner as will be described in greater detail hereinafter. It will be appreciated that second section 78 may have other shapes other than the spherical shape shown so long as the second section 78 serves to retain the stem member 14 within the stalk member 16.

Figure 2:
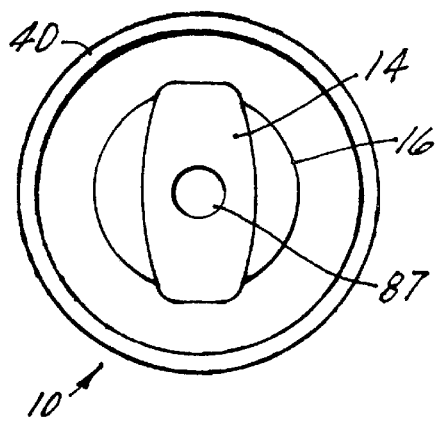
FIG. 2 is a cross sectional view of the earplug of FIG. 1 taken along the line 2—2.
Figure 3:
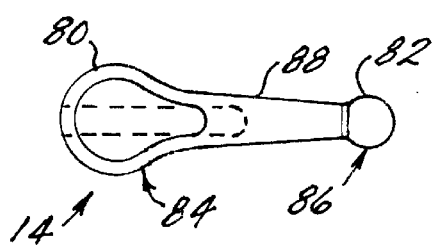
FIG. 3 is a cross. sectional view of an exemplary earplug stem for use in the earplug according to the present invention.

Referring now to FIGS. 1—3, the stem member 14 comprises an elongated member having a first end 80 and an opposing second end 82. The stem member 14 is generally formed of a paddle portion 84 at the first end 80, a retaining portion 86 at the second end 82, and a tapered shaft 88 extending between the paddle portion 84 and the retaining portion 86. The paddle portion 84 has a generally arcuate shape which leads into the tapered shaft 88 wherein the tapered shaft 88 has a width greater than a width of the tapered shaft 88 at the point where the tapered shaft 88 joins the retaining portion 86. The shaft 88 is generally tapered about 10° which permits the shaft 88 to be both stiff when the stem member 14 is pushed into the ear and flexible to take the bend of the ear canal after insertion without excess pressure on the ear canal. The paddle portion 84 is shaped to fit between the fingers comfortably so that the user may grip the earplug 10 and insert the earplug 10 into the ear of the user.

In an exemplary embodiment, the retaining portion 86 comprises a ball portion of a given diameter and in one exemplary embodiment, the diameter is about 0.150 inches. The ball portion 86 is designed to eliminate the narrow end of the stem taper. Therefore, the diameter of the ball portion 86 is preferably greater than the diameter of the shaft 88 where shaft 88 joins ball portion 86. The ball portion 86 also provides a safety feature as the ball portion 86 provides a technique to secure the stem member 14 within the stalk member 16. It is within the scope of the present invention that the second end 82 of the stem member 14 may take shapes other than the ball-like configuration shown so long as the shape of the to second end 82 serves to retain the stem member 14 within the stalk member 16. The paddle portion 84 preferably includes an opening 87 (FIG. 2) formed in an end thereof for holding an attachment cord for holding a pair of earplugs 10 together. The design of the stem member 14 and the taper thereof and the stiffness thereof permits the stem member 14 to be inserted deeper into the ear canal with the earplug 10 feeling less stiff in the ear. More specifically, the paddle portion 84 is designed to permit easy insertion and removal of the earplug 10 from the ear of the user and the tapered design of the stem member 14 permits the stem member 14 to be both stiff when the earplug 10 is being inserted into the ear canal and yet flexible so that the stem member 14 may take the bend of the ear canal after insertion without excess pressure on the ear canal. More specifically, the configuration of the stem member 14 of the present invention permits the stem member 14 to exhibit decreasing stiffness from the first end 80 to the junction of the first and second sections 76, 78 where the retaining portion 86 is formed.

As illustrated in FIGS. 1—3, the stem member 14 is received and secured within the stem channel 70 during use of the earplug 10. It will be appreciated that the stem member 14 is releasably secured within the stem channel 70 in that the stem member 14 may be removed and inserted therein. However, the removeability of the stem member 14 from the stalk member 16 is not a critical aspect of the present invention. As previously described, the stem member 14 is initially received within the stem channel 70 by inserting the ball portion 86 into the entrance 72 of the stem channel 70 and then directing the ball portion 86 into the stem channel 70 until the ball portion 86 seats within the second section 78 of the stem channel 70 at second end 74. Because the ball portion 86 is complementarily sized and shaped as the second section 78, the second section 78 acts as a stop for the stem member 14 and also securely retains the stem member 14 within the stalk member 16. The tapered shaft 88 is likewise complementarily shaped and sized as the first section 76 of the stem channel 70 so that the tapered shaft 88 seats within the first section 76 of the stem channel 70 when the stem member 14 is inserted into the stalk member 16 of the earplug 10.

As illustrated, the thickness of the material forming the stalk member 16 is generally uniform around the stem channel 70 from the end of the second section 78 to the entrance 72 of the first section 76. This permits the stem member 14 to be properly supported within the stalk member 16 when the stem member 14 is inserted into the stalk member 16. Thus, the stalk member 16 has a tapered design similar to the tapered design of the stem channel 70.

The stem member 14 may be formed of any suitable material. However, the material used to form the stem member 14 is preferably selected from the materials having a glass transition in the temperature range of about 50° F. to about 100° F. and more preferably from about 80° F. to about 100° F. This softening characteristic of the stem member 14 allows the stem member 14 to soften (relax after insertion) when in the ear causing the relieving of excess pressure in the ear. One such material that is preferred for use in forming the stem member 14 of the earplug 10 is a polyvinyl chloride material. One particularly preferred material is a polyurethane based shape memory polymer. This material undergoes noticeable property changes in hardness, flexibility, and elastic modulus when the temperature of the material is changed. An exemplary polyurethane based shape memory polymer is commercially available from Mitshubishi Heavy Industries, Ltd. under the tradename "Shape Memory Polymer", MM20 series. This particular polymer exhibits the property of changing from a rigid plastic to a rubbery plastic when the temperature is raised to the glass transition point.

FIG. 2 is a cross sectional end view of the earplug 10 of FIG. 1 and is otherwise self-explanatory.

Figure 4:
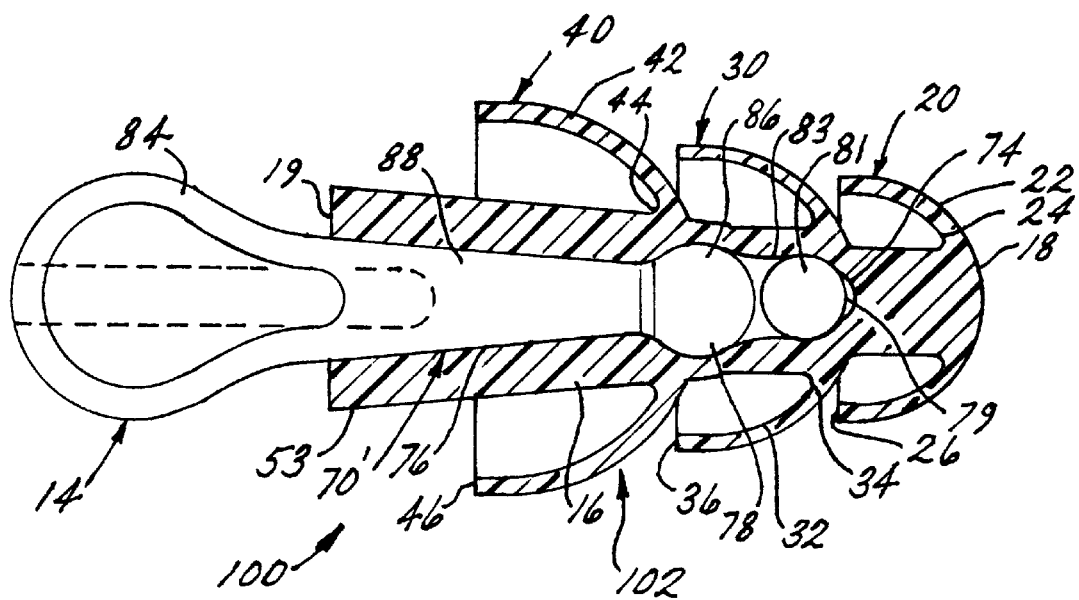
FIG. 4 is a cross sectional view of an earplug according to a second embodiment of the present invention.

Now referring to FIGS. 3—4 in which a second embodiment of the present invention is illustrated with reference to FIG. 4. An earplug according to the second embodiment of the present invention is generally indicated at 100. Earplug 100 is similar to earplug 10 with like elements being numbered alike. The earplug 100 broadly comprises a body 102 and the stem member 14. The body 102 is similar to body member 12 with the exception that the stem channel 70' is modified so that it includes a detectable insert compartment 79 at the second end 74 of the stem channel 70'. In the first embodiment, the second end 74 of the stem channel 70' is positioned proximate the trailing edge 36 (FIG. 1) of the flange element 30, while the second end 74 marked by the third section 79 (a detectable insert compartment) of the stem channel 70' is located proximate the trailing edge 26 of the first flange element 20. In other words, the depth of the stem channel 70' is greater in the second embodiment relative to the flange elements 20, 30, and 40 than in the first embodiment. The third section 79 and the second end 74 in the second embodiment is proximate the trailing edge 26 of the flange element 20.

More specifically, the stem channel 70' includes the first section 76 and the second section 78 and also in the second embodiment, the stem channel 70' includes the third section 79 which defines the compartment. The third section 79 is formed at the second end 74 and is located proximate the second section 78 so that the second section 78 provides an entrance into the third section 79. Second end 74 is rounded so that the third section 79 is designed to receive a detectable insert 81 which in this embodiment is a detectable ball formed of magnetic stainless steel. The detectable ball 81 is disposed first within the stem channel 70' by inserting the ball 81 until the ball 81 seats within the third section 79 against at least a portion of the second end 74. An exemplary ball 81 is disclosed in commonly assigned U.S. patent application Ser. No. 09/226,467, which is hereby incorporated by reference in its entirety.

The second section 78 and the third section 79 have a neck 83 formed therebetween so that once the ball 81 is pushed past the neck 83, the ball 81 will rest within the third section 79 and because the diameter between the neck 83 is less than the diameter of the ball 81, the ball 81 is prevented from freely moving back into the second section 78. The diameter of the third section 79 is approximately equal to the diameter of the ball 81 which results in the ball 81 being securely held within the third section 79. From the neck 83, the width of the second section 76 increases so as to permit the ball portion 86 of the stem member 14 to be frictionally retained therein.

Referring now to FIGS. 1—4. Preferably, the selection of the resilient polymeric material utilized in the fabrication of at least the skirts 22, 32, and 42 of the flange elements 20, 30, and 40 is made in light of attaining the benefits of the earplug 10 of the present invention. The resilient polymeric material should have a Shore A Durometer hardness value (by the technique of ASTM 2240-81) of between about 10 and about 90, and preferably, of between about 30 and about 60. The stalk member 16 can, of course, be formed of a resilient polymeric material of the same type employed for the skirts 22, 32, and 42, or if desired, can be composed of a resilient polymeric material having a somewhat higher Shore A Durometer hardness value. For example, the stalk member 16 may be formed of a material having a Shore A Durometer of up to about 100. In one exemplary embodiment of the present invention, the material used to fabricate the stalk member 16 has a Shore A Durometer hardness value of between about 70 and about 90. In another preferred embodiment of the present invention, however, for the purposes of easy fabrication, it is preferred to utilize a single polymeric material for the entirety of the construction.

It will be appreciated that there are many known resilient polymeric materials which may be utilized effectively in the fabrication of the earplugs 10 of the present invention. For example, natural rubber, neoprene rubber, SBR rubber, silicone rubber, EPDM rubber, polybutadiene rubber, polyurethane elastomers, ethylene vinyl acetate elastomers, elastomers based on acrylic acid precursors and vinyl halide polymers are all generally suitable materials of construction which can generally be procured from various commercial sources with the desired Shore A Durometer values or which can be suitably compounded (such as by internal and/or external plasticizing thereof) so as to confer the necessary desired hardness values thereto. Particularly preferred polymeric materials are the thermoplastic silicone rubber compositions such as exemplified by a family of thermoplastic injection moldable elastomers sold under the trademark, C-FLEX®, Concept Polymer Technologies, Inc., Clearwater, Fla. These silicone rubber compositions are available in a considerable range of Shore A Durometer hardness values, can be thermally formed into intricate shapes by any conventional thermoplastic molding technique and the wares produced therefrom can generally be sterilized or cleansed without degradation thereof. Another preferred material for use in the construction of earplugs 10 of the present invention is a thermoplastic SBR block copolymer such as those produced by and marked in a number of grades under the brand name, KRATON, by Shell Chemical Company, Synthetic Rubber Division, NY, N.Y.

Figure 5:
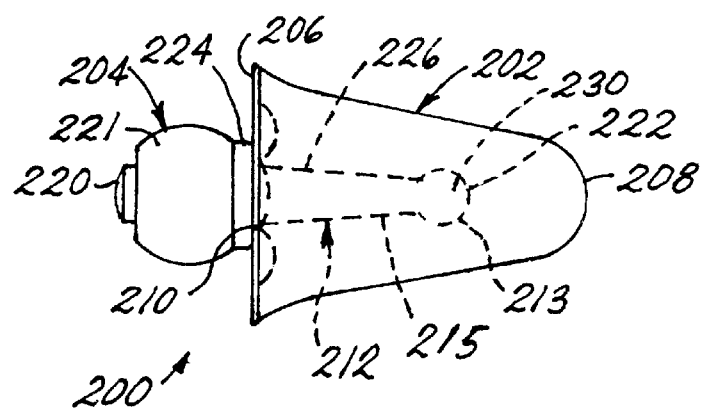
FIG. 5 is a cross sectional view of an earplug according to a third embodiment of the present invention.

Now referring to FIG. 5 in which another embodiment of the present invention is illustrated. In this embodiment, an exemplary earplug is generally indicated at 200. The earplug 200 includes a body 202 and a stem member 204. The body 202 may be formed from any number of suitable materials and may take any number of suitable shapes. For example, many of the externally and internally plasticized polymeric foams disclosed in commonly assigned U.S. Re. Pat. No. 29,487 are generally suitable for use as a material of construction of the present earplug 200. These plasticized polymeric foams are slow recovery foams which are not only comfortable, but also have been shown to deliver high-in-field noise protection at all frequencies. Other suitable materials are disclosed in commonly assigned U.S. Pat. No. 5,203,352 to Gardner which discloses a dynamically stiff foam material having a low static stiffness and a high dynamic stiffness which provides improved attenuation. For example, the foam component preferably has a dynamically spring constant of at least about 300 pounds per inch and a dynamic loss factor of at least about 0.25. One particularly suitable dynamically stiff foam material is a polyurethane material having the desired characteristics. Additional suitable polyurethane foam formulations are disclosed in U.S. Pat. No. 4,158,087 to Wood, which is hereby incorporated by reference in its entirety. Applicant hereby expressly incorporates in its entirety the contents of U.S. Pat. No. Re. 29,487; U.S. Pat. No. 5,203,352; and U.S. Pat. No. 5,792, 998.

In the exemplary embodiment illustrated in FIG. 5, the body 202 has a first end 206 and an opposing second end 208, wherein the first end 206 is a free end and the second end 208 is a nose end which is inserted into the wearer's ear. The first end 206 has a greater diameter than a diameter of the second end 208 so that the body 202 has a generally tapered design. The free end 206 has an opening 210 formed therein for receiving the stem member 204 and the opening 210 acts as an entrance to a stem channel 212 which is complementarily shaped as the stem member 204 so that the stem member 204 is intimately received therein in a retaining manner.

The stem member 204 is similar to the stem member 14 described hereinbefore. Generally, the stem member 204 includes a first end 220 and an opposing second end 222. The first end 220 comprises a free end which extends beyond the body 202 when the stem member 204 is inserted into the stem channel 212. In the illustrated embodiment, the first end 220 has a first annular section 221 for ease of gripping the stem member 204 and a shoulder section 224 adjacent to the first annular section 221 and a shaft 226 which leads from the shoulder section 224 to a retaining section 230 at the second end 222 thereof. The shaft 226 is similar to shaft 88 of the previous embodiments in that the shaft 226 is tapered in nature and has a greater diameter at the junction between the shaft 226 and the shoulder section 224. The retaining section 222 is designed to retain the stem member 204 within the stem channel 212 and in the illustrated embodiment, the retaining section 222 comprises a spherical (ball) member which is intimately received within an end portion 213 of the stem channel 212 which has a complementary shape as the spherical member 222 so that the stem member 204 is securely inserted and retained within body 202. The stem channel 212 also has a tapered portion 215 which complements the shaft 226 of the stem member 204.

The stem member 204 is formed from the same materials as have been described previously with reference to the stem member 14. More specifically, the stem member 204 is preferably formed of a material having a glass transition in the temperature range of about 50° F. to about 100° F. and more preferably from about 80° F. to about 100° F. When the stem member 204 is inserted into the body 202, the shoulder section 224 abuts against the free end 206 of the body 202 and along with the retaining section 222 serves to locate and position the stem member 204 within the stem channel 212. It being understood that the shape of the body 202 and stem member 204 are merely exemplary in nature and are not intended to limit the scope of the present invention. The present invention may be broadly thought of as teaching an earplug having a body formed of a variety of materials in varying shapes and a stem member which has a predetermined shape and is formed of a preselected material so that the stiffness of the stem member varies and decreases from the free end of the stem member to a point proximate the second end of the stem member where a retaining member is provided to securely retain the stem member within the body of the earplug.

The present invention thus provides an earplug having a stalk body with a stem member extending therefrom. Ease of insertion of the stalk body into an ear canal of the user results because of the design and physical characteristics of the stem member of the present invention. Improved attenuation results because the user is able to insert the earplug of the present invention into the ear canal so that the earplug comfortably takes the bend of the ear canal because of the flexible yet stiff characteristics of the stem member of the present invention. Because the earplug may be properly inserted into the ear canal without excess pressure on the ear canal, the user may easily insert the earplug into the ear canal to the proper depth so that maximum attenuation is achieved.

While preferred embodiments have been shown and described, various modifications and substitutions may be made thereto without departing from the spirit and scope of the invention. Accordingly, it is understood that the present invention has been described by way of illustrations and not limitation.

What is claimed is:

1. A hearing protector earplug, comprising:
   a body having an insertion end and an opposing second end, the body including a stem channel formed therein; and
   a stem member disposed within the stem channel, the stem member comprising a material having a glass transition temperature range between about 50 to about 100 degrees Fahrenheit,.

2. The hearing protector of claim 1, wherein the stem member includes a paddle portion at a first end for gripping of the stem member to insert the earplug within an ear of a user.

3. The hearing protector of claim 1, wherein the second end of the stem member comprises a spherical member designed to securely retain the stem member within the stem channel of the body.

4. The hearing protector of claim 1, wherein an intermediate section of the stem member comprises a tapered shaft having a stiffness which decreases along a length of the shaft in a direction towards a second end of the stem member.

5. The hearing protector of claim 1, wherein the stem member is formed of a material such that insertion of the stem member within an ear of a user results in a decrease in stiffness over a portion of the stem member which is inserted within the ear.

6. The hearing protector of claim 1, wherein the stem member has a first stiffness in an ambient environment and a second stiffness when the stem member is inserted into an ear of a user, the first stiffness being greater than the second stiffness so that the stem member softens when inserted into the ear for added comfort.

7. The hearing protector of claim 1, wherein the body comprises
   an elongated stalk member having a nose end, the stalk member having the stem channel formed therein; and
   a flange array including a plurality of rearwardly extending flange elements integrally affixed to the stalk member at spaced intervals along at least a portion of a length of the stalk member.

8. The hearing protector of claim 7, wherein the flange elements are of a generally hemispherical cross section and of serially increasing diameters.

9. The hearing protector of claim 7, wherein each of the flange elements includes a thin skirt having a substantially uniform thickness of between about 0.008 inch and about 0.050 inch.

10. The hearing protector of claim 9, wherein the each skirt is formed of a resilient polymeric material of construction having a Shore A Durometer hardness value of between about 10 and about 90.

11. The hearing protector of claim 9, wherein the intermediate section of the stem member has a taper of about 10°.

12. The hearing protector of claim 3, wherein the stem channel formed in the body has a first section and a second section, the first section comprising a tapered channel and the second section being formed to intimately receive the second end of the stem member.

13. The hearing protector of claim 1, wherein the stem channel formed in the body has a first section, a second section, and a third section, the third section for receiving a detectable insert, the first section being a tapered channel and the second section being formed to intimately receive a second end of the stem member.

14. The hearing protector of claim 13, wherein the detectable insert comprises a detectable metal ball.

15. The hearing protector of claim 13, wherein the third section and second section are separated by a neck portion, the third section having a first diameter and the neck portion having a second diameter, wherein the first diameter is greater than the second diameter.

16. The hearing protector of claim 1, wherein the stem member is formed of a polyvinyl chloride material having a glass transition between about 50° F. and about 100° F.

17. The hearing protector of claim 1, wherein the body is formed of a polymeric foam material.

18. A hearing protector earplug comprising:
   a body having an insertion end and an opposing second end, the body including a stem channel formed therein; and
   a stem member disposed within the stem channel, the stem member comprising a material such that insertion of the earplug in an ear of a user results in the stiffness of the stem member decreasing such that at least the portion of the stem member inserted into the ear becomes less stiff upon being inserted and positioned within the ear.

19. The hearing protector of claim 18, wherein the stem member includes a paddle portion at a first end for gripping of the stem member to insert the earplug within an ear of a user and includes a retaining member formed at a second end, the retaining member being designed to securely retain the stem member within the stem channel of the body.

20. The hearing protector of claim 19, wherein the stem member includes an intermediate section between the first and second ends, the intermediate section comprising a tapered shaft having a stiffness which decreases along a length of the shaft in a direction towards the second end of the stem member.

21. The hearing protector of claim 18, wherein the stem member is formed of a material having a glass transition between about 50° F. and about 100° F.

22. The hearing protector of claim 18 wherein the stem member has a first stiffness in an ambient environment and a second stiffniess when the stem member is inserted into an ear of a user, the first stiffness being greater than the second stiffniess so that the stem member softens when inserted into the ear for added comfort.

23. The hearing protector of claim 18, wherein the body comprises
   an elongated stalk member having a nose end, the stalk member having the stem channel formed therein; and
   a flange array including a plurality of rearwardly extending flange elements integrally affixed to the stalk member at spaced intervals along at least a portion of a length of the stalk member.

24. The hearing protector of claim 18, wherein the body is formed of a polymeric foam material.

25. The hearing protector of claim 6, wherein the first stiffness is between about 50 and 90 Shore A Durometer hardness and wherein the second stiffness is between about 10 and 50 Shore A Durometer hardness.

26. The hearing protector of claim 1, wherein the stem member is formed of a material having a glass transition temperature between about 70 degrees Fahrenheit and about 95 degrees Fahrenheit.

27. The hearing protector of claim 22, wherein the first stiffness is between about 50 and 90 Shore A Durometer hardness and wherein the second stiffniess is between about 10 and 50 Shore A Durometer hardness.

28. The hearing protector of claim 18, wherein the stem member is formed of a material having a glass transition temperature between about 70 degrees Fahrenheit and about 95 degrees Fahrenheit.

* * * * *